(12) United States Patent  (10) Patent No.: US 8,451,449 B2
Holland  (45) Date of Patent: May 28, 2013

(54) OPTICAL REAL-TIME SOIL SENSOR

(76) Inventor: Kyle H. Holland, Lincoln, NE (US)

( * ) Notice: Subject to any disclaimer, the term of this patent is extended or adjusted under 35 U.S.C. 154(b) by 195 days.

(21) Appl. No.: 12/914,415

(22) Filed: Oct. 28, 2010

(65) Prior Publication Data

US 2011/0102798 A1    May 5, 2011

Related U.S. Application Data

(60) Provisional application No. 61/256,748, filed on Oct. 30, 2009.

(51) Int. Cl.
*G01N 21/55* (2006.01)

(52) U.S. Cl.
CPC ..................................... *G01N 21/55* (2013.01)
USPC .......................................... 356/445; 356/446

(58) Field of Classification Search
CPC ...................................................... G01N 21/55
USPC .................................................. 356/445–448
See application file for complete search history.

(56) References Cited

U.S. PATENT DOCUMENTS

| 5,038,040 | A * | 8/1991 | Funk et al. ............... 250/339.02 |
| 5,044,756 | A * | 9/1991 | Gaultney et al. ............... 356/446 |
| 5,789,741 | A | 8/1998 | Kinter et al. |
| 6,570,999 | B1 * | 5/2003 | Monson ........................ 382/109 |
| 6,937,939 | B1 * | 8/2005 | Shibusawa et al. ............. 702/22 |
| 7,058,197 | B1 | 6/2006 | McGuire et al. |
| 8,135,178 | B2 | 3/2012 | Hendrickson et al. |
| 2002/0024665 | A1 * | 2/2002 | Masten .......................... 356/328 |
| 2002/0039186 | A1 * | 4/2002 | Rosenberg .................... 356/432 |
| 2002/0131046 | A1 * | 9/2002 | Christy et al. ................ 356/445 |
| 2006/0158652 | A1 * | 7/2006 | Rooney et al. ................ 356/406 |

OTHER PUBLICATIONS

Girma, Kefyalew et al., "Nitrogen Accumulation in Shoots as a Function of Growth Stage of Corn and Winter Wheat", Journal of Plant Nutrition, Dec. 1, 2010, 34:2, 165-182.
Hodgen, P. J. et al., "Relationship Between Response Indices Measured In-Season and at Harvest in Winter Wheat", Journal of Plant Nutrition, 2005, 28: 221-235.
Holland, K. H. et al., "Derivation of a Variable Rate Nitrogen Application Model for In-Season Fertilization of Corn", Agronomy Journal, 2010, vol. 102, Issue 5, pp. 1415-1424.
Raun, William R. et al., "Independence of yield potential and crop nitrogen response" Precision Agri., Oct. 2, 2010, DOI 10.1007/s11119-010-9196-z; Springer Science+Business Media, LLC, 2010.

(Continued)

*Primary Examiner* — Michael P Stafira
(74) *Attorney, Agent, or Firm* — McKee, Voorhees & Sease, P.L.C.

(57) ABSTRACT

A light sensing apparatus for measuring the reflectance of sub surface soil in real-time while attached to a moving vehicle is disclosed. Reflectance measurements from the apparatus can be related to the organic matter content of the soil. The apparatus is housed in a corrosion resistant enclosure having field rebuildable wear surfaces. The wear surfaces help extend the life of the apparatus by isolating the apparatus's main enclosure from soil abrasion. The wear surfaces also assist in conditioning the sensed soil surface by smoothing the surface prior to sensing. Signal conditioning circuitry in the apparatus is utilized to reject the influence of ambient light in the advent that the soil/apparatus interface opens. A digital processor or other "intelligent controller" is utilized in the apparatus to auto calibrate the apparatus in real-time and/or use predetermined tables or mathematical relationships in order to convert reflectance information into organic matter measurements.

23 Claims, 7 Drawing Sheets

OTHER PUBLICATIONS

Raun, William R. et al., "Chapter 10—Temporally and Spatially Dependent Nitrogen Management for Diverse Environments" c10.indd, Jan. 22, 2009, pp. 203-214.

Shanahan, J.F. et al., "Responsive in-season nitrogen management for cereals", Computers and Electronics in Agriculture 61 (2008) pp. 51-62.

* cited by examiner

OPTICAL REAL-TIME SOIL SENSOR

CROSS-REFERENCE TO RELATED APPLICATIONS

This application claims priority under 35 U.S.C. §119 to provisional application Ser. No. 61/256,748 filed Oct. 30, 2009, herein incorporated by reference in its entirety.

BACKGROUND OF THE INVENTION

1. Field of the Invention

This invention relates to soil content sensors, and more particularly, to an apparatus for sensing the organic matter content of soil for the purposes of creating soil maps and of varying agricultural products including but not limited to herbicides, fertilizer and seeds.

2. Problems in the Art

The organic matter content of a soil is a significant variable in modern soil management and relates to a soil's adsorption of pesticides, its water holding capacity, and its yield potential are often related to its organic matter content. By sensing a landscape's organic matter content in real-time, the potential of applying agricultural products without the use of preprocessed maps will allow producers to optimize their use as well as maximizing profitability.

Conventional agricultural equipment is designed to apply chemicals and plant crops at uniform rates within a field, regardless of changes in soil type or organic matter content. This can result in an over application of chemicals in some areas of the field, an under application in other areas, overplanting in some areas and under planting in others. It would therefore be desirable to provide a prescription application system which would rapidly and accurately adjust chemical and seeding rates by sensing variations in soil type and organic matter as equipment traverses a field. There is thus a need for an apparatus that will sense the organic content of soil as chemicals are being applied or crops planted so that the application of the chemicals or the seeding can be adjusted based upon the sensed organic matter content of the particular area of the field to be treated or planted. In the past couple decades, there has been interest in developing agricultural equipment capable of sensing soil organic matter content and adjusting the corresponding application rate of herbicides, seeds or fertilizer as the equipment moves across the field. Such sensing systems require knowledge of the mathematical relationship between organic matter content and soil color. In general, progress in developing such sensor systems has proven to be unsatisfactory because the developers have attempted to develop universal relationships between organic matter content and sensor output. The problem with this approach is that it is known that different soil associations can have different relationships between organic matter content and soil color. Another problem faced in developing an accurate real-time soil organic matter sensor is that the scene, i.e., particular area of the soil that is being observed by the sensor, must have a generally uniform surface. These sensors typically work by reflecting light off the scene. If the surface of the scene is not uniform, the reflectance will vary in response to surface roughness changes yielding erroneous results. Variations in the surface of the scene can be caused by differences in soil texture, size of the soil aggregates, moisture content, etc. Ambient light can also adversely affect the accuracy of such sensors by introducing a second, variable source of light which is also reflected from the scene and picked up by the sensor.

It is an object, feature, or advantage of the present invention to provide an apparatus for sensing the organic matter content of soil on a real-time basis.

It is another object, feature, or advantage of the present invention to provide an apparatus for sensing the organic matter content of soil that auto calibrates itself while being pulled through the field.

It is a further object, feature, or advantage of the present invention to provide a means to rebuild/service the wear surfaces of the apparatus in the field.

It is a still further object, feature, or advantage of the present invention to provide an apparatus for sensing the organic matter content of soil that is immune to influence of ambient light.

It is another object, feature, or advantage of the present invention to provide a soil sensor that reduces problems caused by variations in soil moisture and surface roughness.

One or more of these and/or other objects, features, or advantages of the present invention will become apparent from the Specification and claims that follow. No single embodiment need exhibit all or any of these objects, features, and advantages.

BRIEF SUMMARY OF THE INVENTION

The apparatus preferably includes a member that prepares the surface of the soil scene immediately before it is observed by the sensor to provide a generally uniform surface, i.e., generally flat and smooth. One embodiment of the apparatus senses subsurface soil reflectance at depths typically ranging from 10 cm to 25 cm while another embodiment of the apparatus senses the freshly tilled surface remotely (non contact) from a distance of 3 cm to 50 cm (or greater) distance from the soil surface. Further, the light source preferably comprises solid-state emitters that are arranged in proximity to a photodiode or array of photodiodes. The soil is sensed through a scratch resistant transparent material that is in contact with the soil surface in the case of the subsurface sensor or above the surface in the case of the noncontact embodiment. The apparatus also preferably includes a processor that processes the light sensed by the light sensor to determine the organic matter content of the soil at the soil scene. The processor in some embodiments uses an average organic matter content value determined by a soil sampling service provider and auto calibrates the sensor as it is pulled through the field. In other embodiments, the processor has data reflecting an experimentally determined characterization of the soil in the local geographic area where the soil being sensed is located. This data comprises a mathematical equation for different classes of soils, e.g., a linear regression equation for soils having a low sand content and a curvilinear regression equation for soils with a relatively higher sand content. Further, each such equation has parameters which are determined from the particular landscape where the apparatus is used. The processor uses the appropriate mathematical equation to solve for the organic matter content of the soil using the sensed reflected light as an input to the equation.

Conceptually, a system for close range remote sensing of soil color, including the soil itself, can be characterized as having four basic components—an illumination device, a scene, a sensor, and an algorithm processor. The illumination device is illustratively an active light source that illuminates the soil scene. The desired information is contained in the spectral variations of the electromagnetic energy emanating from the scene. The sensor collects the energy and measures its features. The processor will implement an auto calibration algorithm using a field or landscape's average organic matter content as a single input value or for initialization, or a deterministic algorithm which will make an appropriate estimation based on feature measurements provided by the output from the sensor. As will be discussed in more detail later, the apparatus of this invention senses the magnitude of light, illustratively provided from a solid state light source, that is, reflected from the scene and determines the organic matter content based on the magnitude of the reflected light.

The apparatus may be used for creating soil maps or for varying the application rate of an agricultural product or seed rate of a landscape. Typically, the apparatus will be interfaced to an agricultural controller that is used to collect and variably apply an agricultural product. Communication between apparatus and agricultural controller is performed via a serial communication bus.

According to one aspect of the present invention, a sensor for measuring organic matter content of soil includes a replaceable wear surface, a corrosion resistant enclosure, and a light source for illuminating the soil with light. There is at least one photo detector to receive reflected light from the soil. There is also a scratch resistant optical window in contact with the soil, wherein the optical window allows light from the light source to illuminate the soil and the reflected light emanating from the soil to reach the at least one photo detector.

According to another aspect of the present invention, a sensor for measuring organic matter content of soil includes a corrosion resistant enclosure, and a light source for illuminating the soil at a distance with light. There is at least one photo detector to receive reflected light from the soil. There is also a scratch resistant optical window wherein the optical window allows light from the light source to illuminate the soil and the reflected light emanating from the soil to reach the at least one photo detector.

According to another aspect of the present invention, a method for measuring organic matter content of soil is provided. The method includes moving a sensor through a field. While moving the sensor through the field, the method includes illuminating the soil with light from a light source passing through an optical window of the sensor in contact with the soil. While moving the sensor through the field, the method includes receiving reflected light through the optical window of the sensor at least one photodetector. The method also includes processing a signal from each of the at least one photodetector to determine the organic matter content of the soil.

According to another aspect of the present invention, a system for use in measuring organic matter content of soil is provided. The system includes a soil sensor. The soil sensor includes: (a) a replaceable wear surface, (b) a corrosion resistant enclosure, (c) a light source for illuminating the soil with light, (d) at least one photo detector to receive reflected light from the soil, and (e) a scratch resistant optical window in contact with the soil, wherein the optical window allows light from the light source to illuminate the soil and the reflected light emanating from the soil to reach the at least one photo detector. The system further includes a phase detection circuit operatively connected to the at least one photo detector. The system further includes an analog-to-digital converter operatively connected to the phase detection circuit. The system also includes an intelligent control operatively connected to the analog-to-digital converter.

According to another aspect of the present invention, a system for use in measuring organic matter content of soil is provided. The system includes a soil sensor. The soil sensor includes: (a) a corrosion resistant enclosure, (b) a light source for illuminating the soil with light, (c) at least one photo detector to receive reflected light from the soil, and (d) a scratch resistant optical window, wherein the optical window allows light from the light source to illuminate the soil and the reflected light emanating from the soil to reach the at least one photo detector. The system further includes a phase detection circuit operatively connected to the at least one photo detector. The system further includes an analog-to-digital converter operatively connected to the phase detection circuit. The system also includes an intelligent control operatively connected to the analog-to-digital converter.

According to another aspect of the present invention, a method for measuring organic matter content of soil is provided. The method includes moving a sensor through a field. While moving the sensor through the field, the method provides for illuminating the soil with light from a light source passing through an optical window of the sensor in contact with the soil. While moving the sensor through the field, the method provides for receiving reflected light through the optical window of the sensor at least one photodetector. The method further provides for determining reflectance at a plurality of different wavelengths for the light, normalizing the reflectance to provide a normalized reflectance to reduce sensitivity to variations in water content of the soil, and determining the organic matter content of the soil using the normalized reflectance.

According to another aspect of the present invention, a method for determining organic matter content of soil is provided. The method includes moving a sensor through a field, while moving the sensor through the field, illuminating the soil with light from a light source, while moving the sensor through the field, receiving reflected light, determining reflectance associated with the reflected light, and determining the organic matter content of the soil using the reflectance through use of an auto-calibrated algorithm.

BRIEF DESCRIPTION OF THE DRAWINGS

Additional features and advantages of the invention will become apparent to those skilled in the art upon consideration of the following detailed description of typical embodiments, exemplifying the best modes of carrying out the invention as presently perceived. The detailed description particularly refers to the accompanying figures.

DETAILED DESCRIPTION OF THE PREFERRED EMBODIMENTS

Chemical and physical properties vary from soil to soil and affect the reflectance and absorption characteristics of each soil. Color is an obvious soil property and can be used as an indirect measure of other soil characteristics. Soil is a heterogeneous substance and thus has a variety of different factors that affect reflectance. The reflectance of electromagnetic energy and the factors that attenuate the amplitude of the electromagnetic energy reflected from a soil surface must be considered in an appropriate sensor design. The factors affecting soil reflectance are texture, moisture content, surface roughness, iron oxide content, and organic matter content.

Variations in moisture content are much more severe at surface level than beneath the soil surface. At the surface level, moisture can vary exceedingly due to differential drying of the surface, residue cover, and changes in topography. Beneath the soil surface, however, moisture content is more uniform and at a level where a slight variance in moisture content might not significantly affect reflectance. Subsequently, the apparatus has been designed specifically to sense soil beneath the soil's surface or to sense a freshly worked soil surface at time of planting, tilling, seeding, etc.

A major variable affecting soil reflectance is the surface roughness. The energy reflected from a soil surface is decreased by increased surface roughness. Surface roughness tends to be more of a problem at closer ranges due to a smaller sampling area. The rough surface diffuses light over a larger scene than is normally viewed by the sensor. Using a multiple wavelengths of light when sensing can minimize the effect of surface roughness for noncontact sensors such as disclosed as one embodiment.

Surface roughness is predominately determined by soil tillage practices. A minimum tillage practice tends to create a rougher surface than conventional tillage practice where larger soil aggregates are reduced in size by increased tillage processes. Thus, it is important to provide for some minimum amount of soil conditioning to produce a uniform, constant surface when attempting to determine the organic matter content of soil by light reflectance, regardless of any previous tillage of the soil.

Figure 1:
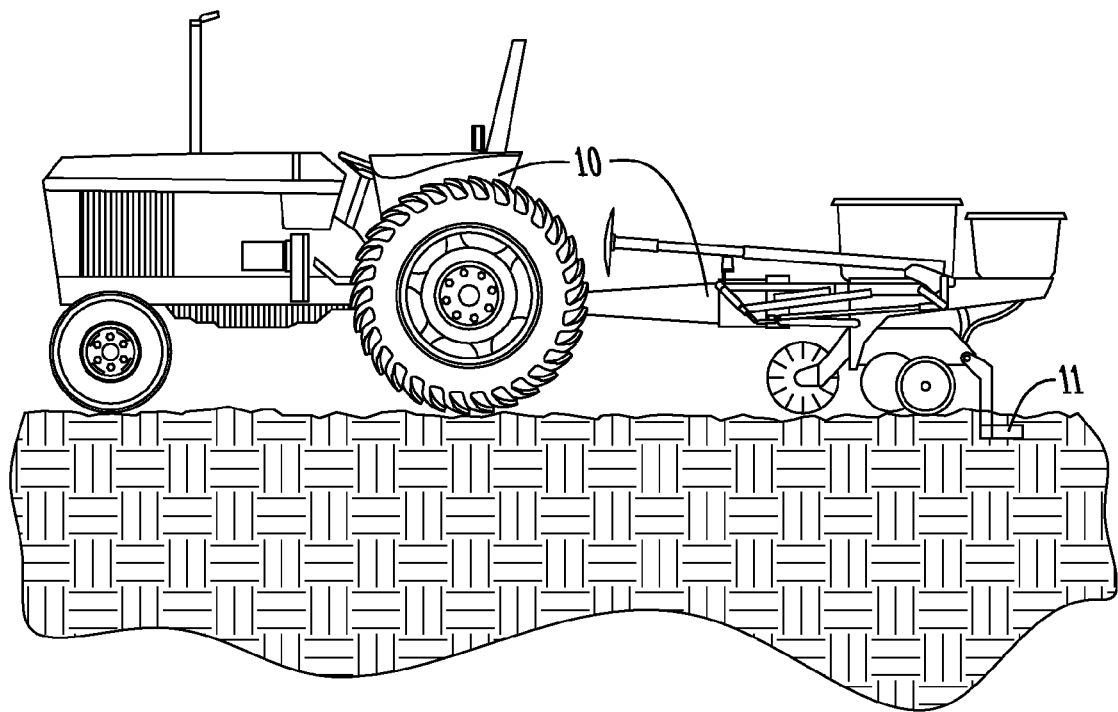
FIG. 1. Diagram of sensor pulled through field by tractor while mounted to agricultural implement.
Figure 2:
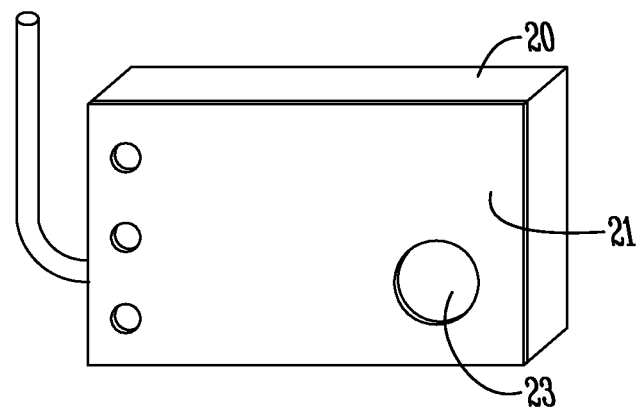
FIG. 2. Diagram of sensor enclosure having a replaceable wear plate.
Figure 3:
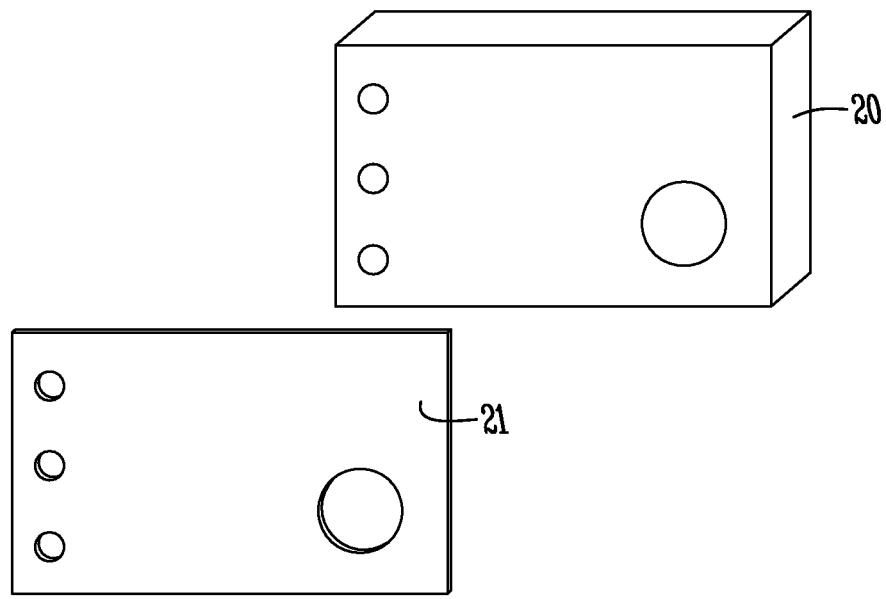
FIG. 3. Diagram of sensor with wear plate separated from corrosion resistant body.

In practice, the sensor apparatus 11 will be connected to a piece of agricultural equipment 10 and pulled through a field as shown in FIG. 1. The sensor 11 will be positioned by the operator so as to measure soil reflectance at a preferred depth of about 10 to 25 cm under the soil surface. FIG. 2 shows a diagram of the sensor enclosure. The sensor enclosure 20 will most preferably be made of a corrosion resistant metal (stainless steel, aluminum, etc.) or plastic material (teflon, pvc, polyethelene, etc.). The enclosure facilitates the protection of the electronic circuitry while providing optical emission and reception port 22 for the light source and the light detector components, respectively, of the sensor. A unique feature of the enclosure pertains to a field rebuildable wear surface also referred to as a field replaceable wear surface 21. The wear surface is intended to increase the longevity of the sensor enclosure by limiting abrasion to the enclosure. This wear surface is intended to be maintained by the operator on an annual basis. The material for this wear surface can be metal (steel, stainless steel, etc.) or plastic (Teflon, UHMW polyethelene, etc.) and can be fastened to the enclosure body 20 with adhesives and/or fastening hardware such as screws. FIG. 3 shows the enclosure with the wear surface 21 separated from enclosure 20. The optical port 22 in FIG. 2 is covered by a hard, transparent window. This window can be made of various types of optical materials to protect the emitter and detector electronics. The optical material should have a mohs hardness greater than 6. Materials meeting this hardness requirement include, but not limited, to quartz and sapphire. To those skilled in the art it should be readily apparent that the sensor optics can take on many forms.

Figure 8:
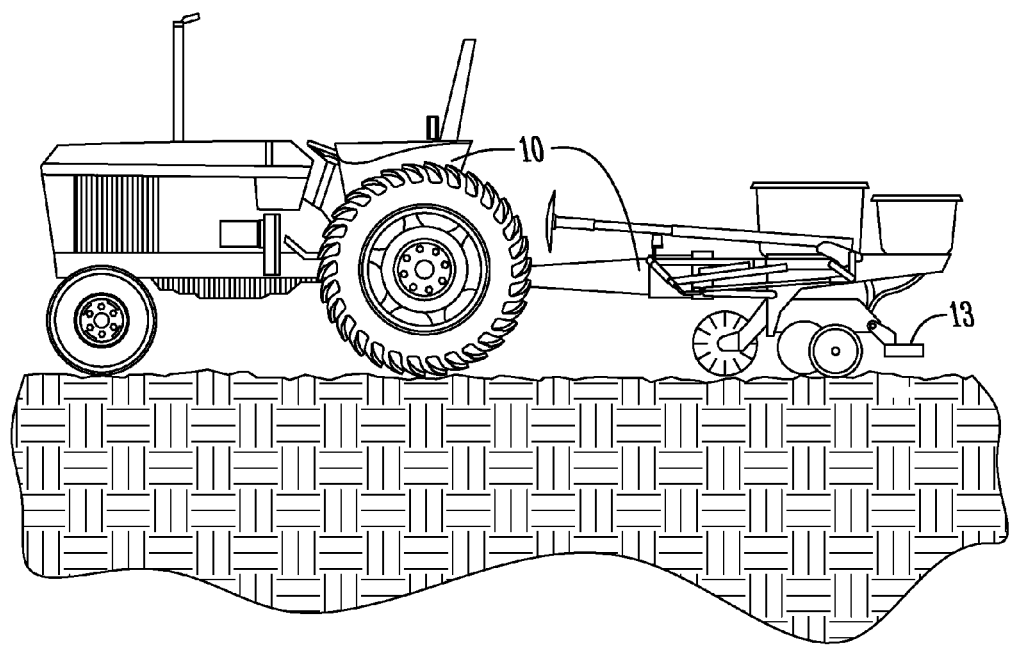
FIG. 8. Diagram of noncontact sensor 13 above the soil surface.

Additionally, the sensor apparatus 81 will be connected to a piece of agricultural equipment 80 and driven over a field as shown in FIG. 8. The sensor 11 will be positioned by the operator so as to measure soil reflectance of freshly worked soil at a preferred distance of about 3 to 50 cm above the soil surface. FIG. 9 shows a diagram of the sensor enclosure. The sensor enclosure 90 will most preferably be made of a corrosion resistant metal (stainless steel, aluminum, etc.) or plastic material (teflon, pvc, polyethelene, etc.). The enclosure facilitates the protection of the electronic circuitry while providing optical emission and reception port 92 for the light source and the light detector components, respectively, of the sensor. The optical port 22 in FIG. 2 is covered by a hard, transparent window. This window can be made of various types of optical materials to protect the emitter and detector electronics. The optical material should have a mohs hardness greater than 6. Materials meeting this hardness requirement include, but not limited, to quartz and sapphire. To those skilled in the art it should be readily apparent that the sensor optics can take on many forms. Plastics mab used but may be prone to scratching during cleaning. If plastic materials are used, the optical windows will be replaceable in the event of scratching or clouding from cleaning operations.

Figure 4:
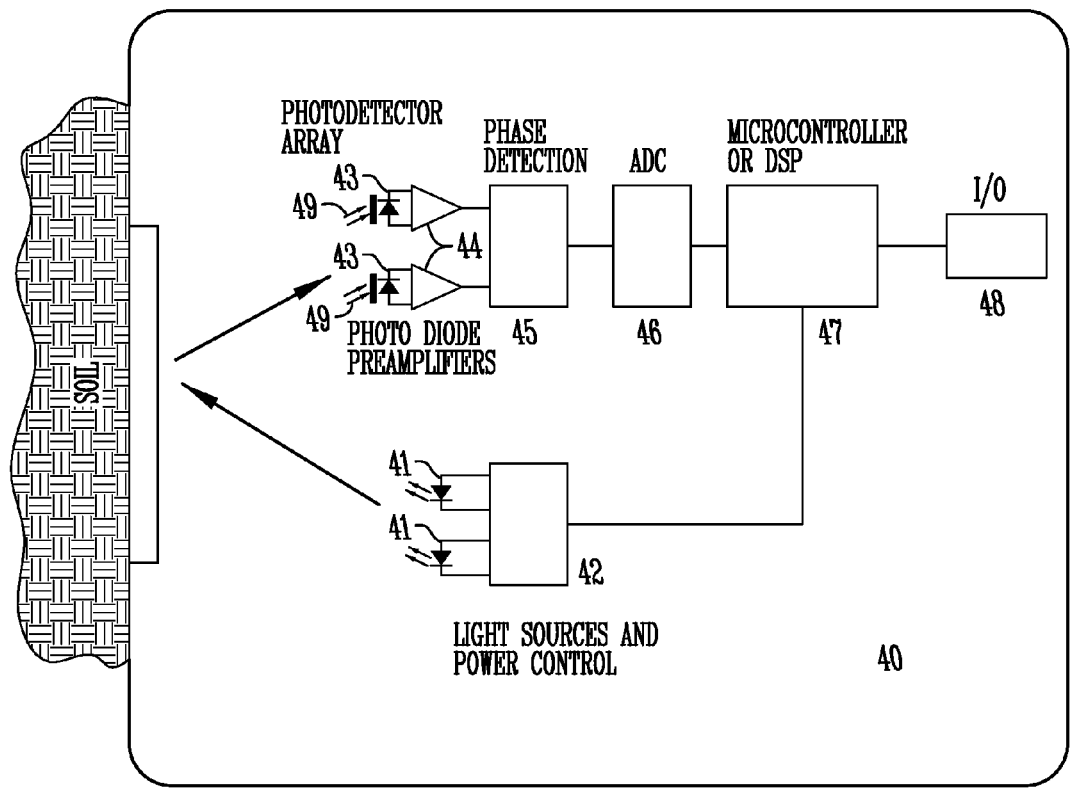
FIG. 4. Sensor electronics block diagram.

FIG. 4 shows a system diagram typical for the many embodiments of the invention. The sensor 40 is composed of optics to facilitate optical energy collimation and collection, a modulated light source 41 comprised of one or many banks of polychromatic LEDs and/or monochromatic LEDs or laser diodes (LD) with associated modulated driver and power control electronics 42, one or more photodetectors 43, high-speed preamplifier circuitry with ambient light cancellation 44, a phase sensitive signal conditioning 45 and data acquisition circuitry 46, and a microcontrol unit (MCU) or digital signal processor (DSP) 47 and an input/output interface 48 to communicate sensor data to an operator or controller. These system elements will be discussed in the following. Some embodiments will require spectral or specular band shaping/filtering. This function is performed using element 49.

The light source for the invention is most preferably composed of light emitting diodes or laser diodes. LEDs are convenient light sources for this type of invention for a number of reasons. First, LEDs are available in a number of colors useful for making soil reflectance measurements. LEDs are readily available in colors spanning from deep violet (395 nm) to near infrared (940 nm). Most recently, the UV LEDs have been developed in the 350 nm to 370 nm. These particular devices might be useful for stimulating fluorescence in soil. Another useful class of LEDs has been recently developed for the telecommunications industry. These devices have spectral emissions spanning from approximately 600 nm to 1550 nm. This range of devices is particularly useful for measuring water absorption bands in soil. Second, LEDs are extremely easy to use and can be modulated to megahertz frequencies. Relatively simple electronic driver circuits can be implemented and easily controlled by sensor controller electronics. Last, LEDs have long lifetimes and are rugged. The typical monochromatic LED will operate between 80,000 and 100,000 hours depending on the quiescent device power and operating temperature range.

Another useful type of LED is the phosphor coated LED. Phosphor coated LED's are convenient light sources for this type of invention for a number of reasons. First, white light emitting LED's are available that have spectral emission characteristics that are useful for making soil color measurements. These LED's can be constructed to have color temperatures that span from deep violet (400 nm) to near infrared (900 nm). Second, white light LED's using phosphor coatings over UV or blue LED emitters can have lifetimes of 40,000 to 80,000 hours.

Most white light emitting LED's in production today are based on an InGaN—GaN structure, and emit blue light of wavelengths between 450 nm-470 nm blue GaN. These GaN-based, InGaN-active-layer LED's are covered by a yellowish phosphor coating usually made of cerium-doped yttrium aluminum garnet (Ce3+:YAG) crystals which have been powdered and bound in a polymer or silicone adhesive. The LED chip emits blue light, part of which is efficiently converted to a broad spectrum centered at about 580 nm (yellow) by the Ce3+:YAG. The emission color of Ce3+:YAG emitters can be modified by substituting the cerium with other rare earth elements such as terbium and gadolinium and can even be further adjusted by substituting some or all of the aluminum in the YAG with gallium. Due to the spectral characteristics of the diode, the red and green colors of objects in its blue yellow light are not as vivid as in broad-spectrum light. Manufacturing variations and varying thicknesses in the phosphor make the LED's produce light with different color temperatures, from warm yellowish to cold bluish. Spectrum of a white LED clearly showing blue light which is directly emitted by the GaN-based LED (peak at about 465 nanometers) and the more broadband stokes shifted light emitted by the Ce3+:YAG phosphor which extends from around 500 to 700 nanometers. White LEDs can also be made by coating near ultraviolet emitting LEDs with a mixture of high efficiency europium based red and blue emitting phosphors plus green emitting copper and aluminum doped zinc sulfide (ZnS:Cu, Al). This is a method analogous to the way fluorescent lamps work. The spectrum of a white LED is easily modified to create other colors by modifying the elemental components in the phosphor coating. For example, an orange, broad-band LED can be created to emit longer wavelengths of light—higher intensities of red and NIR—by using a phosphor coating containing a mixture of gadolinium, aluminum, oxygen and cerium ($Gd_3Al_5O_{12}$:Ce) over a 470 nm LED die. It should be noted that there are numerous other methods, that one skilled in the art, can create different spectral outputs for LED devices (using green, yellow and red phosphor compounds) having the basic structure of the white phosphor LED.

Figure 7:
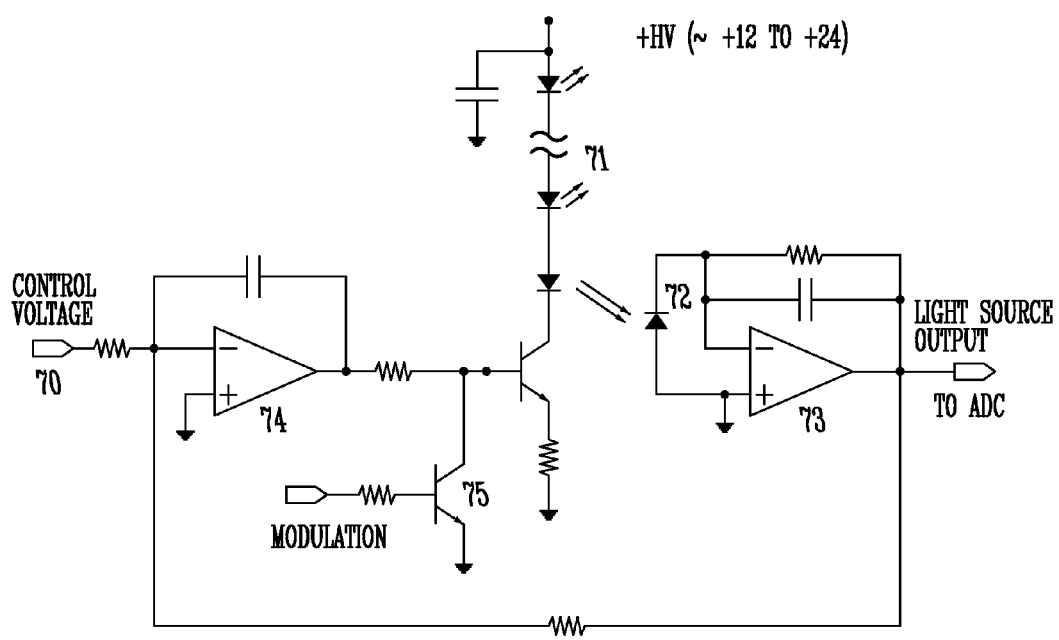
FIG. 7. Temperature compensation circuitry for LED output intensity control.

The output intensity of LEDs is very temperature dependent. Depending on the material type, an LEDs output can drift between 0.4%/C and 1%/C. A decrease in output intensity, even it is being monitored and corrected via calculation, can result in diminished signal to noise performance of the measurement. FIG. 7 shows schematically a circuit that provides active power control for the light source and an output intensity signal for monitoring and calibration. Control voltage 70 sets the output power of light source 71. Photodiode 72, an Infineon SFH203 (Munich, Germany), samples part of the output intensity of light source 71 and feeds this signal via amplifier 73 to servo amplifier 74. Modulation of the output signal is performed using transistor 75. Furthermore, the output of amplifier 73 can be utilized to monitor the light source intensity for purposes of calibration and diagnostics. The performance of this circuit has provided output intensity control of approximately 0.05%/C over the operating range of the invention. When a polychromatic source is utilized, photodiode 76 and amplifier 77 incorporated into the circuit so as to monitor the IR output of the light source. Suitable photodiodes in this case would be a SFH203FA for photodiode 76 and a SFH203 for photodiode 72. Both diodes are manufactured by Infineon (Munich, Germany). Many techniques have been discussed in literature detailing methods on maintaining and stabilizing light sources for photometric type measurements including the method presented here.

The photodetectors used in the invention are most preferably silicon photodiodes however other detector technologies such as GaAsP, InGaAs, GaP, and the like, may be utilized as well. The choice in a particular photodetector is determined by the type of light source chosen for the sensor. Silicon detectors have a typical photosensitivity spanning from 200 nm (blue enhanced) to 1200 nm. When using narrow band light sources, no additional spectral filtering or band shaping is usually necessary. However, when using broadband light source like white LED's spectral filtering or band shaping is required. Band shaping of the detectors is performed using filtering materials such as colored filter glass, interference filters or dichroic filters. Additionally, some embodiments of the invention may utilize polarizing filters to minimize the impact specular reflectance on the measured signal so as to better measure diffuse reflectance from the soil.

As will be apparent to one skilled in the art, various combinations of the aforementioned filter techniques can be combined in order to band-shape the radiation impinging on the photodetector surface.

The output from the photodetector (or photodetector array) 43 in FIG. 4 is amplified using a transconductance amplifier with a feedback servo to cancel the effects of ambient light. The composite amplifier acts as an AC amplifier that allows only modulated reflectance signals resulting from the modulated light source to pass on to the later stages of the sensor's instrumentation. DC or slowly varying light signals are not amplified and are rejected by the sensor photodetector conditioning circuitry. This is important in situations where the sensor/soil interface may open and allow sunlight to reach the photodetector. In this situation, the influence of sunlight is rejected and amplifier circuitry does not saturate.

Referring once again to FIG. 4, the invention utilizes a phase sensitive detector circuit (PSD) 45 and analog-to-digital converter 46 (ADC) after each photodetector. The PSDs, also refer to as a lock-in amplifiers, are utilized by the invention to extract and further amplify the very small signal detected and amplified by the photodetector preamplifiers. PSDs are often used in applications where the signal to be measured is very small in amplitude and buried in noise. Detection is carried out synchronously with modulation of the light source. Phase sensitive detection is one of many types of band narrowing techniques that can be utilized to measure small signals. As will be apparent to those skilled in the art, other methods include the use of averaging techniques, discriminators and direct digital conversion/processing. With respect to direct digital conversion/processing, the phase sensitive acquisition component can be performed internally to a MCU or DSP by directly sampling the output of the photodiode amplifiers and performing the bandpass and PSD functions digitally. By performing these operations in the digital domain, the temperature drift of the phase detector, common to analog techniques, can be eliminated. The invention performs the synchronous modulation/demodulation at a carrier frequency of 10 kHz. It should be noted that the operation of the invention is not limited to this particular modulation rate and can operate at other modulation as well with as much effectiveness. Additionally, this rate can be increased or decreased as dictated by the application. The MCU or DSP samples the output of a PSD 45 utilizing ADC 46. The resolution of the ADC is most preferably greater than 12 bits. Each channel can sampled using a dedicated ADC or one ADC can be utilized to sample all channels via a multiplexer.

Once the detected optical signals are amplified, demodulated and quantified, the MCU or DSP 47 can calculate the soil's organic matter content based on the reflectance values sensed. It is important to minimize the influence of moisture on the reflectance signature of the soil. The invention accomplishes this by using normalizing, in particular, normalizing the reflectance at a particular wavelength with respect to slope of the soil reflectance curve. This is primarily accomplished using a difference of two or more wavelengths in the denominator of a ratio based expression. The equation utilized is shown below:

$$MCR1 = \frac{\rho_{\lambda 1}}{\rho_{\lambda 1} - \rho_{\lambda 2}}, \quad \lambda 1 > \lambda 2$$

where

MCR1 is the moisture compensated reflectance, $\rho_{\lambda 1}$ is the reflectance at first wavelength ($\lambda 1$) and $\rho_{\lambda 2}$ is the reflectance at second wavelength ($\lambda 2$)

In some embodiments $\rho_{\lambda 1}$ may represent an NIR reflectance and $\rho_{\lambda 2}$ represents a visible reflectance. In other embodiments $\rho_{\lambda 1}$ and $\rho_{\lambda 2}$ may both be visible band reflectances or infrared reflectances. Another form of the above equation is shown below:

$$MCR2 = \frac{\rho_{\lambda 1} + \rho_{\lambda 2}}{\rho_{\lambda 1} - \rho_{\lambda 2}}, \quad \lambda 1 > \lambda 2$$

where

MCR2 is the moisture compensated reflectance, $\rho_{\lambda 1}$ is the reflectance at first wavelength ($\lambda 1$) and $\rho_{\lambda 2}$ is the reflectance at second wavelength ($\lambda 2$)

Yet another form of the above equation is shown below:

$$MCR3 = \frac{\alpha}{\rho_{\lambda 1} - \rho_{\lambda 2}}, \quad \lambda 1 > \lambda 2$$

where

MCR3 is the moisture compensated reflectance, $\rho_{\lambda 1}$ is the reflectance at first wavelength ($\lambda 1$) and $\rho_{\lambda 2}$ is the reflectance at second wavelength ($\lambda 2$)

$\alpha$ is a constant typically equal to 1.

The common feature of MCR1, MCR2, and MCR3 is the wavelength difference in the denominator of each equation that is utilized to normalize a reflectance or function of reflectances with respect to the slope of the soil characteristic. The variables MCR1, MCR2, and MCR3 can be used as arguments in functions that calibrate the output of the sensor in terms of soil organic matter. In some embodiments the sensor can auto calibrate itself in real-time. The calibration can be performed using a number of methods of which include descriptive statistics and a field's average organic matter content. This average organic matter measurement is typically performed by soil sampling service providers and is based on the average of 8 to 10 soil samples per 40 acre region. Other non real-time methods of calibrating the sensor involve comparing multiple soil samples with sensor measurements to create a linear regression model that relates sensor readings to organic matter. This model can then be loaded into the sensor in order to provide a calibrated output. Another non real-time method involves post calibrating GPS referenced sensor data using GIS software or other computational means and GPS referenced soil samples.

Data calculated by the sensor's processing component is communicated to an operator or system controller via input/output interface 48. When the invention is incorporated into a sprayer or mapping system having several sensors networked together, the I/O interface will most preferably be a networkable serial port such a as RS485 port or CAN 2.0b port.

One embodiment of the sensor uses one or more monochromatic LEDs with each having a different emission spectra and a single detector to receive reflected light from the soil. In this embodiment, each LED is modulated on and off independently with respect to each other and the reflectance from the soil is measured by the photodetector (or photodetector array) and synchronously demodulated. Various colored LEDs can be used to probe different portions of a soils reflectance curve in order to determine soil properties.

A variation of this embodiment uses laser diodes instead of LEDs and yet another variation utilizes cross polarized filters in front of the LEDs and photodetector(s) to reduce the effect of specular reflections.

A variation of the previous embodiment uses a white LED that emits many colors simultaneously and one or more spectrally filtered photodetectors. In this embodiment, the LED is modulated on and off and the reflectance from the soil is measured by a photodetector or photodetector array and synchronously demodulated. Various filters can be in front of the photodetector(s) to probe different portions of a soils reflectance curve in order to determine soil properties.

As one skilled in the art can see, there are numerous variations of the disclosed apparatus that can be built that would still be within the scope of this invention.

Applications of Use-Methods

Figure 5:
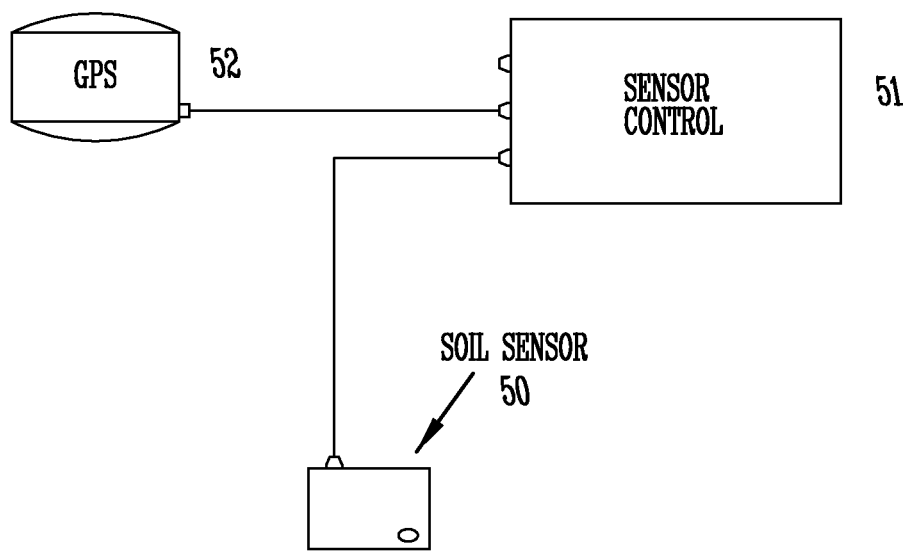
FIG. 5. Sensor utilized as component of mapping system.

FIG. 5 show a block diagram of the invention incorporated into a system that is used to map organic matter content variation within a field. Elements of the system include soil sensor 50, sensor controller 51, and GPS 52. The role of the sensor in this system is to measure the variations in organic matter content based on changes in sensed soil reflectance. Data produced by the sensor is collected by the system controller for storage and later analysis. Each sensor point is geo-referenced using the GPS connected the system controller. There are two primary ways in which mapping can be performed the system. First, the map collected by the system can be all inclusive, that is, every data point measured by the sensor can be stored away in the controller's memory for later retrieval and analysis. Second, the sensor/controller can be programmed with a defined set of rules so as to distinguish low organic matter regions of a landscape from high organic matter regions and vice versa and store only the regions of interest. This mode of operation, sometimes referred to as a scouting mode, saves storage space in the controller and reduces the amount of data processing that has to be performed.

Figure 6:
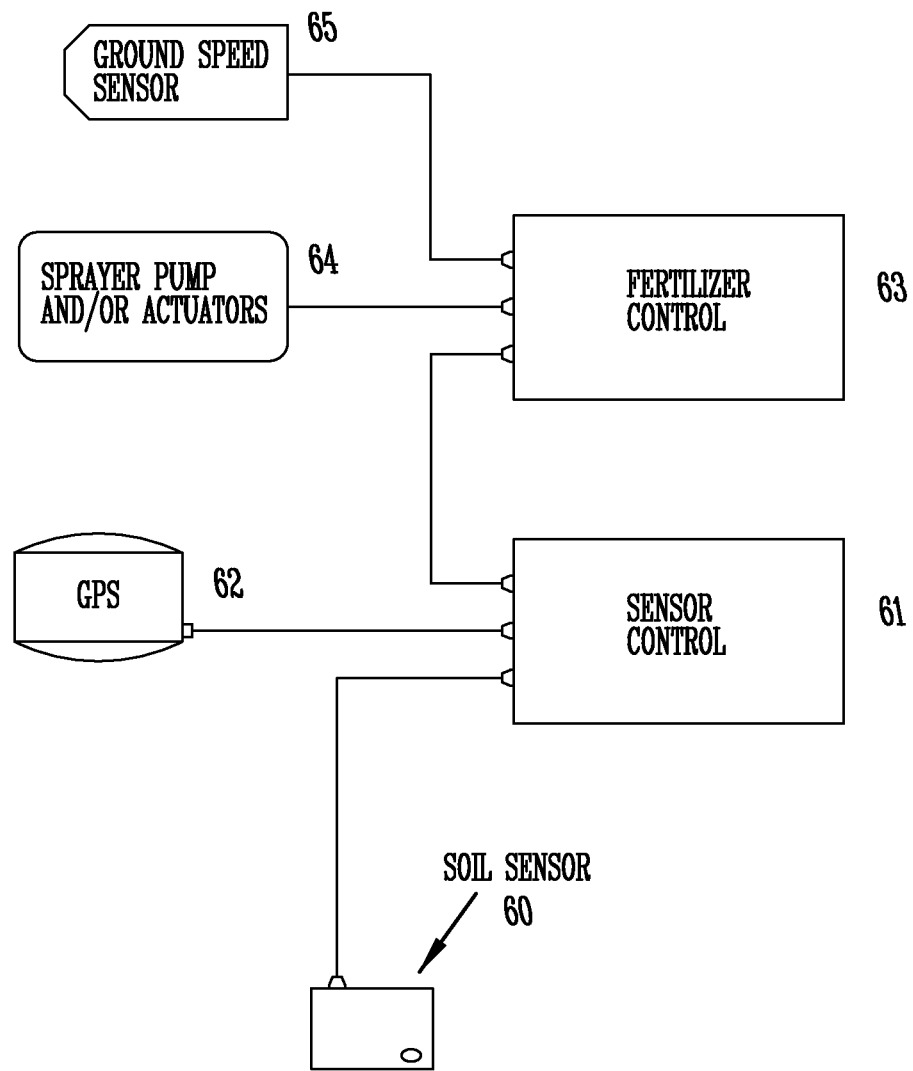
FIG. 6. Sensor utilized as component of variable rate and/or mapping system.

FIG. 6 show a block diagram of the invention incorporated into a system that is used for applying an agricultural product. Elements of the system include soil sensor 60, sensor controller 61, GPS 62, controller 63, sprayer pumps/seed actuators 64 and ground speed sensor 65. The agricultural product may be either in liquid or solid form and may be, but not limited to, a nutrient, mineral, seed, herbicide or fungicide or a combination of the aforementioned materials. GPS can be incorporated in the system when a map is required of soil variation (including organic matter) characteristics for later analysis. In addition to mapping soil characteristics, material dispensation rates can be mapped as well. The benefits of a system such as the one just described are both economic and environmental. By using less fertilizer and only applying it where the crop needs it, the producer can lower his use of fertilizer and thus lower his production cost and by using less fertilizer and only applying it where the crop needs it based on organic matter content, reduced run-off and leaching into our watershed occurs. The organic matter content of the soil is an indicator of the amount of soil N available to the plant. The fertilizer rate that an applicator applies can be varied according to the sensor readings in real-time. Typically, soil organic matter contributes 10 to 30 kg/ha of soil N per percent of organic matter. A simple mathematical relationship that can be utilized by a variable fertilizer controller is shown below in the following equation, $$N_{APP} = N_{NOMINAL} - \alpha \cdot OM\%$$

where $N_{APP}$ is the fertilizer application rate varied by the controller, $N_{NOMINAL}$ is the flat fertilizer rate the producer would normally apply to the field, α is a coefficient that scales the applied fertilizer rate based on organic matter content and OM % is the organic matter content as determined or sensed by the disclosed apparatus.

Similarly, seeding rate can be modified based on organic matter content. Certain portions of a field do not yield as well as other portions due to the soil composition and in part this is indicated by the organic matter content of this region. As such, using a flat seeding rate across the field can result in lower returns because excess seed may be planted in portions of the field that do not have the fertility to support plant growth at high seed populations. In this case it is sometime desirable to decrease the seed rates in areas of the field that have low organic matter contents. A simple method to vary the seed rate of a planter is to use a threshold test as shown below:

$$S_{RATE} = \begin{Bmatrix} 20{,}000 \text{ if } OM \% < 1.2\% \\ 26{,}000 \text{ if } OM \% > 1.2\% \end{Bmatrix}$$

Where $S_{RATE}$ is the seed rate of the planter and

OM % is the organic matter content as determined or sensed by the disclosed apparatus.

In the above example, only a single threshold was utilized. Note however, multiple thresholds may be utilized to further optimize seed rate variation across an agricultural landscape.

While only a limited number of embodiments of the present invention have been disclosed herein, it will be readily apparent to persons skilled in the art that numerous changes and modifications may be made thereto without departing from the spirit of the invention. Accordingly, the foregoing disclosure and description thereof are for illustrative purposes only and do not in any way limit the invention which is defined only by the following claims.

REFERENCES

The following references are herein incorporated by reference in their entirety:

| U.S. Patent Documents | | |
|---|---|---|
| Re35100 | November 1995 | Monson et al. |
| 3,464,504 | September 1969 | Strange |
| 3,502,543 | March 1970 | Sewell |
| 3,593,809 | July 1971 | Derry |
| 4,266,878 | May 1981 | Auer |
| 4,284,150 | August 1981 | Davis |
| 4,332,301 | June 1982 | Jonell |
| 4,333,541 | June 1982 | Duty |
| 4,482,021 | November 1984 | Repski |
| 4,630,773 | December 1986 | Ortlip |
| 4,685,339 | August 1987 | Philipenko |
| 4,828,047 | May 1989 | Rogerson |
| 4,998,590 | March 1991 | Wells |
| 5,033,397 | July 1991 | Colburn, Jr. |
| 5,038,040 | August 1991 | Funk et al. |
| 5,044,756 | September 1991 | Gaultney et al. |
| 5,076,372 | December 1991 | Hellbusch |
| 526169 | May 1993 | Heller |
| 529869 | March 1994 | Huang et al. |
| 5,310,462 | May 1994 | Chen |
| 5,332,480 | July 1994 | Datta et al. |
| 5,355,815 | October 1994 | Monson |
| 5,366,601 | November 1994 | Jones et al. |
| 5,453,924 | September 1995 | Monson et al. |
| 5,461,229 | October 1995 | Sauter et al. |
| 5,467,271 | November 1995 | Abel et al. |
| 5,548,115 | August 1996 | Ballard |
| 5,561,516 | October 1996 | Noble et al. |
| 5,587,538 | December 1996 | Bratton |
| 5,887,491 | March 1999 | Monson et al. |
| 5,950,741 | September 1999 | Wright et al. |
| 601676 | January 2000 | Hale |
| 6,119,531 | September 2000 | Wendte et al. |
| 6,237,429 | May 2001 | Melnyk |
| 6,260,633 | July 2001 | Machek et al. |
| 6,360,829 | March 2002 | Naber et al. |
| 6,766,865 | July 2004 | Dagel et al. |
| 6,959,245 | October 2005 | Rooney et al. |
| 2005/0172733 | August 2005 | Drummond et al. |

Other References

Barnes, E. M. and M. G. Baker. Multispectral Data for Mapping soil texture Possibilities and Limitations. Amer. Soc. Agric. Eng., 16 (6), 731-741 (2000).

Bowers, S. A. and R. J. Hanks. Reflection of Radiant Energy from Soils. Soil Science. 100 (2) 60-68 (1965).

Fernandez, R. N., D. G. Schultze, D. L. Coffin, and G. E. Scoyoc. Color, Organic Matter, and Pesticide Adsorption Relationships in a Soil Landscape. (July-August 1988), Soil Science of America Journal.

Griffis, C. L. "Electronic Sensing of Soil Organic Matter", Trans. Amer. Soc. Agric. Eng., 28:703-705 (1985).

Hoffer, R. M., "Biological and Physical Considerations in Applying Computer-Aided Analysis Techniques to Remote Sensor Data", Remote Sensing: The Quantitative Approach, Chapt. 5 (1978).

Hummel, J. W., K. A. Suddth and S. E. Hollinger. Soil moisture and organic matter prediction of surface and subsurface soils using NIR soil sensor. Computers and Electronics in Agriculture. 32, 185-193 (2001).

Krishman, P., B. J. Bulter, J. Hummel. Close-Range Sensing of Soil Organic Matter. Trans. Amer. Soc. Agric. Eng., 24:306-311 (1981).

Mahgold, G., "New Tool Prescribes Precise Nitrogen Needs", Soybean Digest, p. 16b-16c (February 1988).

Shields, J. A., E. A. Paul, R. J. St. Arnaud and W. K. Head, "Spectrophotometric Measurement of Soil Color and Its Relationship to Moisture and Organic Matter", Can. J. Soil Sci., vol. 48, pp. 271-280 (1968).

Suddth, K. A. and J. W. Hummel. Portable Near Infrared Spectrophotometer for Rapid Soil Analysis. Amer. Soc. Agric. Eng., 36(1), 185-193 (1993).

Suddth, K. A. and J. W. Hummel. Geographic Operating Range Evaluation of a NIR Soil Sensor. Amer. Soc. Agric. Eng., 39(5), 1599-1604 (1995).

Tools with Eyes. Mid-March 1989. Farm Journal. pp. 16-18.

What is claimed is:

1. A method for measuring organic matter content of soil, the method comprising:

providing a sensor for measuring organic matter content of soil, the sensor comprising: (a) a replaceable wear surface; (b) a corrosion resistant enclosure;

(c) a light source for illuminating the soil with light;

(d) at least one photo detector configured to receive reflected light from the soil;

(e) a scratch resistant optical window in contact with the soil, wherein the optical window allows light from the light source to illuminate the soil and the reflected light emanating from the soil to reach the at least one photo detector;

measuring organic matter content of soil with the sensor by determining reflectance at a plurality of different wavelengths of light and normalizing the reflectance to provide a normalized reflectance and determining the organic matter content of the soil using the normalized reflectance;

varying application of an agricultural product at least partially based on the organic matter content of the soil; and wherein the measuring organic matter content of the soil and the varying application of the agricultural product being performed in real-time in a single pass.

2. The method of claim 1 wherein the scratch resistant optical window has a mohs hardness greater than six.

3. The method of claim 1 wherein the light source comprises at least one light emitting diode.

4. The method of claim 1 wherein the light source comprises at least one laser diode.

5. The method of claim 1 wherein the providing the sensor is performed by providing an agricultural implement comprising the sensor.

6. A method for measuring organic matter content of soil, the method comprising:

moving a sensor through a field;

while moving the sensor through the field, modulating a light source on and off to thereby provide for illuminating the soil with light from the light source passing through an optical window of the sensor in contact with the soil;

while moving the sensor through the field, receiving reflected light through the optical window of the sensor using at least one photodetector;

processing a signal from each of the at least one photodetector to determine the organic matter content of the soil by determining reflectance at a plurality of different wavelengths of light and normalizing the reflectance and determining the organic matter content of the soil using the normalized reflectance.

7. The method of claim 6 further comprising associating a geoposition with the organic matter content of the soil.

8. The method of claim 6 further comprising varying application of an agricultural product based on the organic matter content of the soil.

9. A method for performing an agricultural production operation in a field, comprising:

measuring organic matter content of soil with a sensor by moving the sensor through the field, illuminating the soil with light from a light source passing through an optical window of the sensor in contact with the soil, receiving reflected light through the optical window of the sensor using at least one photodetector, determining reflectance at a plurality of different wavelengths for the light, normalizing the reflectance to provide a normalized reflectance to reduce sensitivity to variations in water content of the soil, and determining the organic matter content of the soil using the normalized reflectance;

varying application of an agricultural product at least partially based on the organic matter content of the soil; and wherein the measuring organic matter content of the soil and the varying application of the agricultural product being performed in real-time in a single pass;

wherein the sensor comprises: (a) a replaceable wear surface; (h) a corrosion resistant enclosure;

(C) a light source for illuminating the soil with light;

(d) at least one photo detector configured to receive reflected light from the soil; and (e) a scratch resistant optical window in contact with the soil, wherein the optical window allows light from the light source to illuminate the soil and the reflected light emanating from the soil to reach the at least one photo detector.

10. The method of claim 9 wherein the agricultural product comprises seeds.

11. The method of claim 9 wherein the agricultural product comprises chemicals.

12. The method of claim 9 wherein the varying application of the agricultural product comprises actuating at least one actuator.

13. The method of claim 9 wherein the sensor comprises (a) a replaceable wear surface; (b) a corrosion resistant enclosure; (c) a light source for illuminating the soil with light; (d) at least one photo detector to receive reflected light from the soil; (e) a scratch resistant optical window in contact with the soil, wherein the optical window allows light from the light source to illuminate the soil and the reflected light emanating from the soil to reach the at least one photo detector.

14. The method of claim 9 wherein the sensor being configured to measure soil reflectance under a surface of the soil.

15. A method for measuring organic matter content of soil, the method comprising:

providing a system for use in measuring organic matter content of soil, the system comprising:

(1) a soil sensor comprising (a) a replaceable wear surface, (b) a corrosion resistant enclosure, (c) a light source for illuminating the soil with light, (d) at least one photo detector to receive reflected light from the soil, and (e) a scratch resistant optical window in contact with the soil, wherein the optical window allows light from the light source to illuminate the soil and the reflected light emanating from the soil to reach the at least one photo detector;

(2) a phase detection circuit operatively connected to the at least one photo detector;

(3) an analog-to-digital converter operatively connected to the phase detection circuit;

(4) an intelligent control operatively connected to the analog-to-digital converter;

measuring organic matter content of soil with the system;

varying application of an agricultural product at least partially based on the organic matter content of the soil;

wherein the measuring organic matter content of the soil and the varying application of the agricultural product being performed in real-time in a single pass; and wherein the intelligent control is programmed to normalize reflectance.

16. The method of claim 15 wherein the providing the system is performed by providing an agricultural implement comprising the system.

17. The method of claim 15 wherein the intelligent control is programmed to normalize reflectance using an equation having a denominator expressing a difference between reflectance at a first wavelength and reflectance at a second wavelength.

18. A method for measuring organic matter content of soil, the method comprising:
    moving a sensor through a field;
    while moving the sensor through the field, illuminating the soil with light from a light source passing through an optical window of the sensor in contact with the soil;
    while moving the sensor through the field, receiving reflected light through the optical window of the sensor using at least one photodetector;
    determining reflectance at a plurality of different wavelengths for the light;
    normalizing the reflectance to provide a normalized reflectance to reduce sensitivity to variations in water content of the soil; and
    determining the organic matter content of the soil using the normalized reflectance.

19. A method for determining organic matter content of soil, the method comprising:
    moving a sensor through a field;
    while moving the sensor through the field, illuminating the soil with light from a light source;
    while moving the sensor through the field, receiving reflected light;
    determining reflectance associated with the reflected light, wherein the reflectance is a normalized reflectance from reflectances at a plurality of wavelengths;
    determining the organic matter content of the soil using the reflectance through use of an auto-calibrated algorithm.

20. The method of claim 19 wherein the sensor is a non-contact sensor.

21. The method of claim 19 wherein the sensor is a contact sensor.

22. The method of claim 19 wherein the auto-calibration algorithm uses an average organic matter content value for the field.

23. The method of claim 22 wherein the average organic matter content value for the field is used for initialization.

* * * * *

UNITED STATES PATENT AND TRADEMARK OFFICE
CERTIFICATE OF CORRECTION

PATENT NO. : 8,451,449 B2  
APPLICATION NO. : 12/914415  
DATED : May 28, 2013  
INVENTOR(S) : Kyle H. Holland Page 1 of 1

It is certified that error appears in the above-identified patent and that said Letters Patent is hereby corrected as shown below:

In the Claims:

COL. 14, CLAIM 9, LINE 9:
DELETE after face; "(h)"
ADD after face; --(b)--

COL. 14, CLAIM 9, LINE 10:
DELETE "(C)" at beginning of line
ADD --(c)-- at beginning of line Signed and Sealed this
Twenty-third Day of July, 2013

Teresa Stanek Rea
*Acting Director of the United States Patent and Trademark Office*